United States Patent
Koutsoumbelis

(10) Patent No.: US 11,311,317 B2
(45) Date of Patent: Apr. 26, 2022

(54) SPINAL FIXATION DEVICE WITH ROTATABLE CONNECTOR

(71) Applicant: Stelios Koutsoumbelis, Huntington, NY (US)

(72) Inventor: Stelios Koutsoumbelis, Huntington, NY (US)

(\*) Notice: Subject to any disclaimer, the term of this patent is extended or adjusted under 35 U.S.C. 154(b) by 104 days.

(21) Appl. No.: 16/582,069

(22) Filed: Sep. 25, 2019

(65) Prior Publication Data

US 2021/0085372 A1     Mar. 25, 2021

(51) Int. Cl.
*A61B 17/70*     (2006.01)

(52) U.S. Cl.
CPC ............................. *A61B 17/7034* (2013.01)

(58) Field of Classification Search
CPC ........ A61B 17/7032–17/7037; A61B 17/7041; A61B 17/7043; A61B 17/7049–17/7052
See application file for complete search history.

(56) References Cited

U.S. PATENT DOCUMENTS

| | | | |
|---|---|---|---|
| 5,643,263 A | 7/1997 | Simonson | |
| 6,755,830 B2 * | 6/2004 | Minfelde | A61B 17/7035 606/278 |
| 7,648,522 B2 * | 1/2010 | David | A61B 17/7035 606/266 |
| 10,188,431 B2 | 1/2019 | Erbulut et al. | |
| 10,238,429 B2 | 3/2019 | Zhang et al. | |
| 10,307,185 B2 | 6/2019 | Murray | |
| 2002/0138077 A1 | 9/2002 | Ferree | |
| 2002/0193794 A1 * | 12/2002 | Taylor | A61B 17/7038 606/278 |
| 2003/0105460 A1 * | 6/2003 | Crandall | A61B 17/7038 606/256 |
| 2004/0111088 A1 | 6/2004 | Picetti et al. | |

(Continued)

FOREIGN PATENT DOCUMENTS

| | | |
|---|---|---|
| CN | 202 982 193 U | 6/2013 |
| CN | 105 078 562 A | 11/2015 |

OTHER PUBLICATIONS

J. Kenneth Burkus, M.D., "TSRH-3D@ Spinal Instrumentation Surgical Technique," Medtronic Sofamor Danek, 2005, total of 34 pages.

(Continued)

*Primary Examiner* — Julianna N Harvey
*Assistant Examiner* — Holly Joanna Lane
(74) *Attorney, Agent, or Firm* — Collard & Roe, P.C.

(57) ABSTRACT

A spinal fixation device for securing two stabilizing rods to bone has a threaded shaft, a first rod coupling head connected to the threaded shaft and a secondary rod coupling head. The first rod coupling head has a side wall and a cavity with an open top for receiving a rod. In a neutral position of the first rod coupling head, the first rod coupling head extends symmetrically around the longitudinal axis of the threaded shaft. The second rod coupling head is rotatably connected to the first rod coupling head, around an axis of rotation. The axis of rotation is disposed at an angle that is not perpendicular to the longitudinal axis of the threaded shaft when the first rod coupling head is in the neutral position. This allows for two rods to be manipulated independently through different axis planes at any single point of bony fixation.

4 Claims, 3 Drawing Sheets

(56) References Cited

U.S. PATENT DOCUMENTS

| | | |
|---|---|---|
| 2007/0156142 A1* | 7/2007 | Rezach .............. A61B 17/7038 |
| | | 606/252 |
| 2007/0233122 A1 | 10/2007 | Denis et al. |
| 2007/0250061 A1 | 10/2007 | Chin et al. |
| 2008/0021473 A1 | 1/2008 | Butler et al. |
| 2008/0195122 A1* | 8/2008 | Castellvi ............ A61B 17/7041 |
| | | 606/151 |
| 2011/0245883 A1 | 10/2011 | Dall |
| 2013/0090691 A1 | 4/2013 | Zhang et al. |
| 2014/0135839 A1* | 5/2014 | Frankel .............. A61B 17/7043 |
| | | 606/264 |
| 2017/0020573 A1 | 1/2017 | Cain et al. |
| 2017/0035463 A1 | 2/2017 | Harper |
| 2017/0095271 A1* | 4/2017 | Faulhaber ............ A61B 17/705 |
| 2017/0348026 A1 | 12/2017 | Stein et al. |
| 2018/0078284 A1 | 3/2018 | Faulhaber |
| 2018/0228516 A1* | 8/2018 | Armstrong ........... A61B 17/705 |
| 2018/0228518 A1* | 8/2018 | Carruth .............. A61B 17/8685 |
| 2018/0280063 A1* | 10/2018 | Lee .................... A61B 17/7052 |

OTHER PUBLICATIONS

"3CO Procedure featuring Dual Rod Multi-Axial Screw," Surgical Technique, Medtronic, 2019, total of 36 pages.
"CD Horizon™ Solera™ Spinal System with Dual Rod Multi-Axial Screw and Variable Angle Domino," Medtronic, 2019, total of 12 pages.
International Search Report and Written Opinion of the International Searching Authority dated Oct. 21, 2020 in PCT/US20/43666.

* cited by examiner

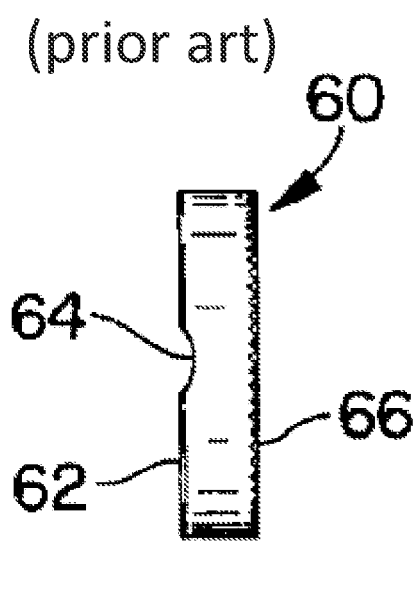
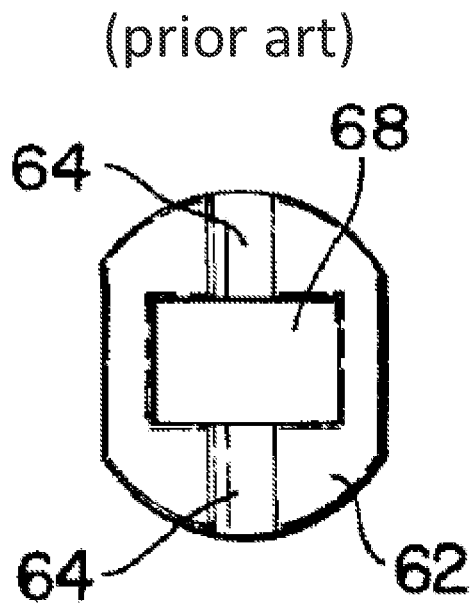
FIG. 2  FIG. 3
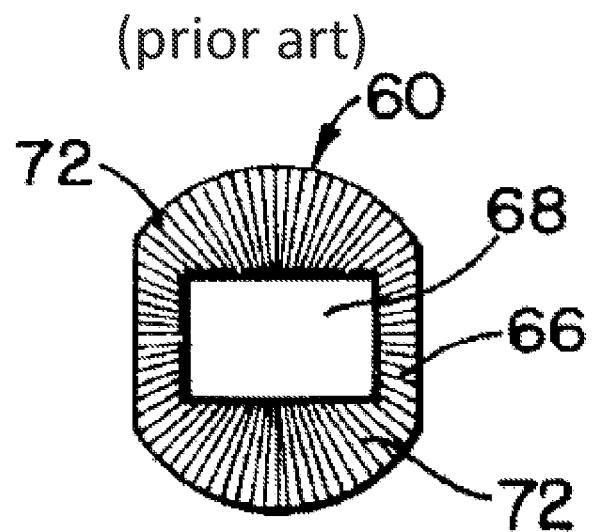
FIG. 4

SPINAL FIXATION DEVICE WITH ROTATABLE CONNECTOR

BACKGROUND OF THE INVENTION

1. Field of the Invention

This invention relates to a spinal fixation device such as a pedicle screw, that is used in spinal surgery including cervical, thoracic, lumbar, pelvic and posterior cranial surgery. In particular, the invention relates to a fixation device (e.g., pedicle screw, lateral mass screw, pelvic bolt, cranial fixation device) having a primary rod-securing element that is rotatably connected to a second rod-securing element having an aperture, so that two rods can be mounted to a single device, and adjustments can be made to the position of the rods with respect to each other.

This allows for the primary rod to be secured in the polyaxial plane, and secondary rod to be secured in the monoaxial plane. This arrangement allows for the highest degree of biomechanical stability, while affording the necessary level of patient safety and surgeon preference. The arrangement of the present invention allows for both primary and secondary rod to be affixed to a single point of bony fixation through said device.

In this description the words pedicle screw, fixation device, spinal implant may all be used interchangeably to describe the invention. The invention can be used throughout the spinal column and in the pelvis and calvarium as well with modifications to the size of implant.

2. The Prior Art

Pedicle screws and securing rods are used in a spinal fusion and spinal fixation to add extra support and strength to the fusion while it heals. This also is used for a variety of reasons, namely whenever rigid fixation in the spinal column is necessary, and surgeon preference. Pedicle screws are placed into spinal segments needed to be fused or stabilized depended upon diagnosis and surgeon preference. In more modern times, this has been extrapolated to include both pelvic and cranial instrumentation. A rod is used to connect the screws, which prevents movement and allows for fixation, whether that be for bony fusion, trauma, tumor. The etiology behind the diagnosis can be degenerative, deformity, trauma, or neoplastic in origin.

The head (connection member) of the typical pedicle screw can be formed as a U- or tulip-shaped element, into which the rod is placed. A set screw is then tightened in the top portion of the tulip to secure the rod to the pedicle screw. It can often be beneficial to used two parallel rods for extra support of the vertebrae. In modern day spinal surgery, there have been reasons for an extra rod of fixation, namely deformity surgery, tumor, trauma, or revision.

Also, the lack of rigidity/increased stability in traditional pedicle screw arrangements has led to bony fusion not healing (pseudoarthrosis) necessitating revision surgery, discomfort to the patient, or hardware failure. There have been several attempts to construct pedicle screws that can be connected to two rods at the same time. For example, US Patent Application Publication. No. 2004/0111088 to Picetti discloses a double-headed pedicle screw, having a single head portion that has a plurality of channels for connected multiple rods. The problem with this and other similar solutions is that the two rods must always be in a fixed positon with each other based on the shape of the head portion. There is no room for adjusting the position or angle of the rods with respect to each other, since the channels in the head are fixed. In addition, the fixed position of the screws does not allow movement of the screws and rods during flexion and extension of the spine. This can create discomfort for the patient. This can also become a problem intraoperatively as it decreases the options to the surgeon for implantation, and can perhaps be incompatible with the patient's surgical anatomy.

Pedicle screws with adjustable pivotable heads have also been developed, such as the ones shown in U.S. Pat. No. 10,188,431 to Erbulut et al. However the heads in this device pivot only around a horizontal axis defined by the posts that secure the heads to the screw. This angle is not ideal, because the top corner of the screw head can cause irritation to the patient during movement, due to its projecting nature. In addition, the angle at which the second head is positioned can be awkward for the surgeon to reach, depending on the position of the surgeon and screw. Namely, this can pose a problem in which said top corner will be compressing upon vital neural elements due to the angle (or lack thereof) in which the second head is in relation to the primary head.

In both aforementioned examples, there are design features that do not allow for ease of use and safety intraoperatively. The chance for the fixation device to conform with a wide variety of patients' surgical anatomy is low at best. Meanwhile, the likelihood for neurologic injury is high secondary to the angles in which primary and secondary rod tulips are oriented.

A connection assembly as disclosed in U.S. Pat. No. 5,643,263 to Simonson has been in use for connecting a rod to a pedicle screw with an adjustable angle. This has proven very useful in practice and it would be desirable to have a system that has this angle adjustability with a capability of attaching two rods at once.

SUMMARY OF THE INVENTION

It is therefore an object of the invention to provide a pedicle screw that allows for a connection of two rods to a single screw, with the connectors for the rods being rotatable relative to each other, and in which the connectors are disposed at an optimal angle for surgical efficiency, patient comfort, and safety.

These and other objects are accomplished by a pedicle screw for securing stabilizing rods to spinal segments or pelvis/cranium, comprising a threaded shaft configured for fastening to bone, and a first rod coupling head connected to the threaded shaft, the first rod coupling head having a side wall and a cavity for receiving a rod. The threaded shaft has a longitudinal axis, and in a neutral position of the first rod coupling head, the first rod coupling head extends symmetrically around the longitudinal axis. The cavity is open toward a top of the first rod coupling head, and has threads at the top into which a set screw is rotated to cover the cavity and fix a rod in the cavity. A second rod coupling head is rotatably connected to the first rod coupling head, around an axis of rotation. The axis of rotation of the second rod coupling head is disposed at an angle α that is not perpendicular to the longitudinal axis of the screw when the first rod coupling head is in the neutral position, so that the second rod coupling head is angled toward the first rod coupling head, rather than being disposed exactly parallel. The optimal angle of tilt is preferably between 5 and 15 degrees off of the perpendicular, or between 70-85 degrees from the longitudinal axis. By having the second rod coupling head being tilted toward the first rod coupling head, the second rod coupling head is more easily accessible to the surgeon during an operative procedure. When reaching over the spine, the tilted rod coupling head is more easily accessible to the surgeon than a parallel arrangement. This leads to more efficient, effective, and safer surgery.

In addition this invention allows the primary rod to be secured through a traditional polyaxial top loaded open tulip (connector), and the secondary rod to be secured through an attached and rotatable closed monoaxial aperture style connector. In this preferred embodiment, the first rod coupling head is connected to the threaded shaft so as be movable polyaxially, at least while the rod is being positioned. A locking plate can be disposed in the first rod coupling head such that inserting a rod in the cavity and tightening a set screw into the rod pushes the rod against the locking plate and prevents any axial movement of the first rod coupling head after the screw is tightened, locking the first coupling head in the neutral position. To accomplish this, the threaded shaft has a ball connector and the first rod coupling head has a socket for receiving the ball connector to connect the first rod coupling head to the threaded shaft in a polyaxial manner. When a set screw is tightened down on the rod, the locking plate is then pressed against the ball connector to prevent any movement of the first rod coupling head around the ball connector once the set screw is fully tightened. One example of a suitable ball connector/locking plate arrangement is disclosed in US Patent Application Publication No. 2017/0020573, the disclosure of which is herein incorporated by reference.

In one embodiment, the second rod coupling head is formed by a connector plate and a C-shaped rod holding element having a cavity for the rod and an aperture for a set screw. The C-shaped rod holding element is fixedly attached to the connector plate. The connector plate is rotatably connected to a side of the first rod coupling head and has a grooved or textured surface that mates with a grooved or textured surface on the first rod coupling head, such that when a rod is inserted through the C-shaped holding element and a set screw is tightened in the aperture, the rod presses the connector plate with its grooved surface against the grooved surface on the first rod coupling head to prevent rotation of the second rod coupling head relative to the first rod coupling head and fix the positions of the rod coupling heads in place.

One advantage of the present invention is that the primary polyaxial coupling head can be used to secure the first rod in sequence with all of the other fixation points cephalad and caudad. Afterwards, the secondary monoaxial coupling head can be manipulated by rotation around a fixed axis to allow for the secondary rod to be safely "threaded" through the connector from screw—to—screw safely around vital neural elements. This would be the standard technique used by spinal surgeons for the increased support of secondary rod supplementation; currently this cannot be achieved as both rods need to be laid down at the same time in a polyaxial manner.

The present invention has the advantage that both rod coupling heads can be adjusted during placement of the rods, and yet are immobile after the set screws are tightened. The present invention allows for the use of a single screw shaft with two adjustable connectors, while in the past, the second connector had to be attached separately down the rod at a remote location. The specific angle of the second rod coupling head in relation to the first rod coupling head allows for safer, more efficient placement of the rods and tightening of the set screws, as it is easier for the surgeon to reach them.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views:

FIG. 2 shows a side view of the connection plate that connects the first and second rod coupling heads;

FIG. 3 shows a front view of the connection plate;

FIG. 4 shows a rear view of the connection plate; and

DETAILED DESCRIPTION OF THE PREFERRED EMBODIMENT

Figure 1:
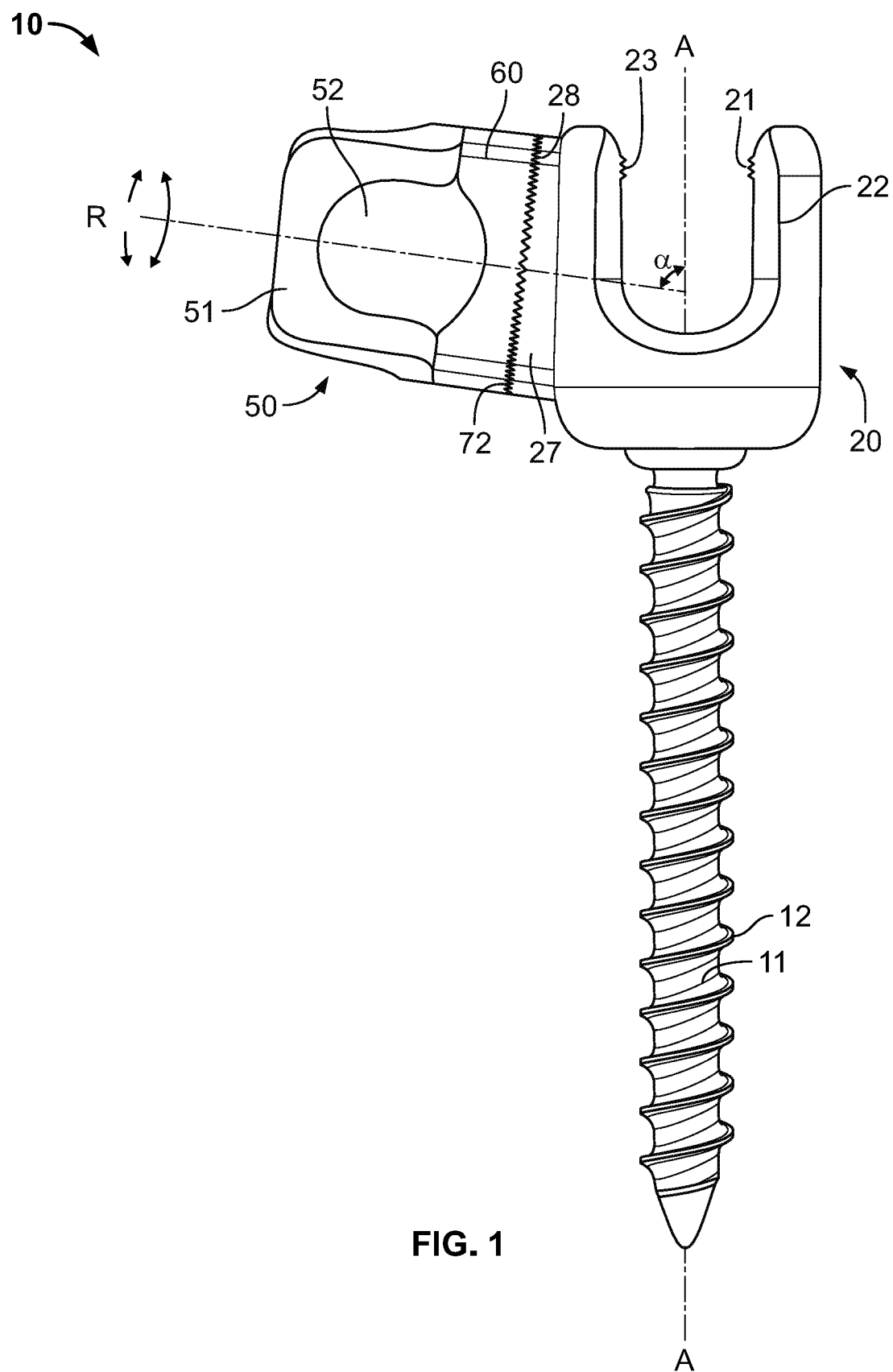
FIG. 1 shows the spinal fixation device according to the invention.

Referring now in detail to the drawings, FIG. 1 shows the pedicle screw 10 according to the invention. Pedicle screw 10 consists of a shaft 11 having helical threads 12 for attaching to bone, a first rod coupling head 20 and a second rod coupling head 50. First rod coupling head 20 is in the form of an open connector, with side walls 22, a cavity 21 for receiving a rod, and threads 23 near a top section for receiving a set screw. Shaft 11 has a longitudinal axis A running through it. Connected to first rod coupling head 20 is a second rod coupling head 50, which is connected to a connector segment 27 of first rod coupling head 20 by a connector plate 60. Connector plate 60 is connected so as to be freely rotatable about an axis of rotation R relative to connector segment 27. Axis of rotation R is not perpendicular to longitudinal axis A, and instead is disposed at an angle α of approximately 83 degrees from axis A, or in a range of preferably 70-85 degrees from axis A. A C-shaped rod holder 51 is fixedly connected to connector plate 60 and together with connector plate 60 forms the second rod coupling head 50, so that second rod coupling head 50 can be rotated relative to first rod coupling head 20. Second rod coupling head 50 has a cavity 52 in the form of a closed aperture into which a second rod can be secured, and a hole for a set screw to secure the second rod to the second rod coupling head 50.

The interior structure of connector plate 60 is shown in FIGS. 2-4. This structure is the same as the one used in U.S. Pat. No. 5,643,263 to connect the structures there, and the disclosure of this patent is herein incorporated by reference.

Connector plate 60 has a front side 62 with an engagement groove 64 for receiving a rod, and a rear side 66, which has a variable angle grooved surface 72. An opening 68 is disposed in the middle of connector plate 60 for connecting connector plate 60 to the first rod coupling head. First rod coupling head 20 has a connector segment 27, with an identical or similar variable angle grooved surface 28 that faces variable angle grooved surface 72, so that when the two surfaces 28, 72 are pressed against each other, rotation of one part relative to the other is prevented due to the frictional contact of the surfaces with each other.

Figure 5:
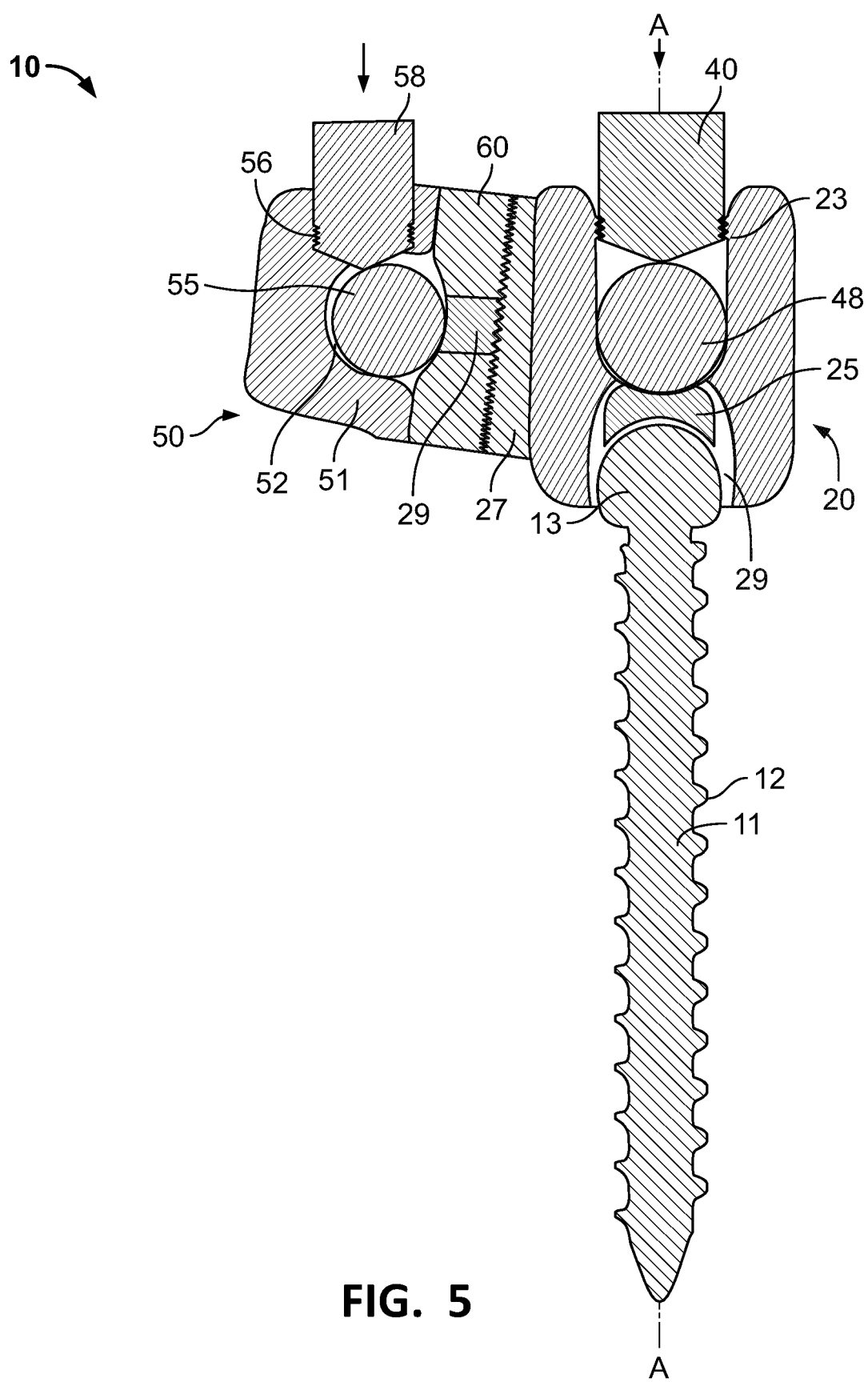
FIG. 5 shows a cross-sectional view of the spinal fixation device in use with rods running therethrough.

The fully assembled pedicle screw 10 is shown in FIG. 5, in cross-section. Here, the interior of first rod coupling head shows that a locking plate 25 is disposed in the bottom of cavity 21. Locking plate 25 abuts a ball head 13 of shaft 11 that is disposed in socket 29, and allows a polyaxial movement of first coupling head 20 relative to shaft 11. Locking plate 25 can be held in place by a spring (not shown). Upon tightening of a set screw 40 in threads 23 of first rod coupling head 20, rod 48 is pressed downward onto locking plate 25, which then presses against ball head 13 and prevents any axial movement of first rod coupling head 20 relative to shaft 11. Upon full tightening of set screw 40, first rod coupling head 20 is locked to shaft 11 in the neutral position, in which first rod coupling head 20 extends symmetrically around the longitudinal axis of shaft 11.

Second rod coupling head 50 is connected via connector plate 60 to holding element 27 of first rod coupling head 20, via an axle element 29 that extends through opening 68 in connector plate 60 and allows connector plate 60 to be freely rotatable relative to connector segment 27 around axis of rotation R when not under stress. In the neutral position of first rod coupling head 20, the axis of rotation R of second rod coupling head 50 is not perpendicular to longitudinal axis A of shaft 11, but rather extends obliquely, at an angle α of between 70-85 degrees to the axis A. A preferred angle α of the axis of rotation R is approximately 83 degrees to the longitudinal axis A, or 7 degrees off of perpendicular.

A second rod 55 is disposed in cavity 52 of second rod coupling head 50, and is held in place by set screw 58, which extends through a hole 56 in holding element 51. Upon tightening of set screw 58, connector plate 60 with its variable angle groove surface 72 is pressed against connector segment 27, and any further rotation of second rod coupling head 50 with respect to first rod coupling head 20 is prevented. Thus, upon tightening of both set screws, the rod coupling heads are fixed in place and no relative movement is permitted. Set screw 58 is loaded from the top down fashion similarly to the primary set screw (set screw 40). Set screw 58 also is slightly angled back toward the primary set screw to allow for safe tightening on to second rod 55. This allows for the pressure needed during this maneuver to be safe and directed away from vital neural elements.

Accordingly, while only a few embodiments of the present invention have been shown and described, it is obvious that many changes and modifications may be made thereunto without departing from the spirit and scope of the invention.

What is claimed is:

1. A spinal fixation device for securing stabilizing rods to bone, comprising;
   a threaded shaft configured for fastening to bone, the threaded shaft having a longitudinal axis, a proximal end and a distal end;
   a first rod coupling head connected to the proximal end of the threaded shaft and being configured to rotate in a polyaxial manner with respect to the threaded shaft, the first rod coupling head having side walls and a first cavity for receiving a first rod, the cavity being open toward a top of the first rod coupling head, wherein in a neutral position of the first rod coupling head, the first rod coupling head extends symmetrically around the longitudinal axis of the threaded shaft; and
   a second rod coupling head being rotatably connected at a first end to one of the side walls of the first rod coupling head, around an axis of rotation so as to rotate in a monoaxial manner with respect to the first rod coupling head, and having a second end opposite the first end, and a second cavity between the first end and the second end that is configured for receiving a second rod;
   wherein when the first rod coupling head is in the neutral position, the axis of rotation is disposed at an angle that is between 70 and 85 degrees from the longitudinal axis of the threaded shaft facing away from the distal end of the threaded shaft, and wherein the axis of rotation intersects the first cavity and extends through a center of the second cavity so that the second rod coupling head rotates symmetrically around the axis of rotation, and wherein when the first rod coupling head is in the neutral position, the second end of the second rod coupling head has a height relative to the longitudinal axis that is not greater than a height of the top of the first rod coupling head.

2. The spinal fixation device according to claim 1, further comprising a locking plate disposed in the first rod coupling head such that inserting the first rod in the first cavity and tightening a set screw into the first rod pushes the first rod against the locking plate and prevents any axial movement of the first rod coupling head to lock the first rod coupling head in the neutral position.

3. The spinal fixation device according to claim 2, wherein the threaded shaft has a ball connector and the first rod coupling head has a socket for receiving the ball connector to connect the first rod coupling head to the threaded shaft in the polyaxial manner.

4. The spinal fixation device according to claim 1, wherein the second rod coupling head is formed by a connector plate and a C-shaped holding element having a the second cavity and together with the connector plate forms a closed aperture for the second rod, the C-shaped holding element having an aperture for a set screw, and the C-shaped holding element being attached to the connector plate, wherein the connector plate is connected to one of the side walls of the first rod coupling head and has a first variable surface that mates with a second variable surface on the first rod coupling head, such that when the second rod is inserted through the C-shaped holding element and the set screw is tightened in the aperture, the second rod presses the first variable surface of the connector plate against the second variable surface on the first rod coupling head to prevent rotation of the second rod coupling head relative to the first rod coupling head.

* * * * *